US011000619B2

(12) United States Patent
Tasz et al.

(10) Patent No.: US 11,000,619 B2
(45) Date of Patent: May 11, 2021

(54) PUMP CONCENTRATED AIR FRESHENER

(71) Applicant: S. C. Johnson & Son, Inc., Racine, WI (US)

(72) Inventors: Maciej K. Tasz, Racine, WI (US); Claudia V. Gamboa, Northfield, IL (US); Alex Mecker, Milwaukee, WI (US); Jeffrey J. Christianson, Oak Creek, WI (US); Kylie L. Levake, Union Grove, WI (US); Christopher P. Wolak, Racine, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 496 days.

(21) Appl. No.: 15/129,672

(22) PCT Filed: Mar. 27, 2015

(86) PCT No.: PCT/US2015/022933
§ 371 (c)(1),
(2) Date: Sep. 27, 2016

(87) PCT Pub. No.: WO2015/148894
PCT Pub. Date: Oct. 1, 2015

(65) Prior Publication Data
US 2017/0173202 A1    Jun. 22, 2017

Related U.S. Application Data

(60) Provisional application No. 61/977,907, filed on Apr. 10, 2014, provisional application No. 61/972,115, filed on Mar. 28, 2014.

(51) Int. Cl.
| *A61L 9/14* | (2006.01) |
| *A61L 2/22* | (2006.01) |
| *A61L 9/01* | (2006.01) |
| *A01N 25/06* | (2006.01) |
| *A01N 31/02* | (2006.01) |

(52) U.S. Cl.
CPC ............... *A61L 9/14* (2013.01); *A01N 25/06* (2013.01); *A01N 31/02* (2013.01); *A61L 2/22* (2013.01); *A61L 9/01* (2013.01); *A61L 2202/26* (2013.01)

(58) Field of Classification Search
CPC ..... A61L 9/14; A61L 2/22; A61L 9/01; A01N 31/02; A01N 25/06
See application file for complete search history.

(56) References Cited

U.S. PATENT DOCUMENTS

| 3,832,459 A | 8/1974 | Berkeley |
| 4,178,264 A | 12/1979 | Streit et al. |
| 4,923,094 A * | 5/1990 | O'Neill ............... B05B 11/3016 222/321.2 |
| 4,938,416 A | 7/1990 | Bertrand et al. |
| 5,047,234 A | 9/1991 | Dickerson et al. |
| 5,547,636 A | 8/1996 | Vick et al. |
| 5,609,168 A * | 3/1997 | Kischka ................. A61K 8/365 132/202 |
| 5,663,134 A | 9/1997 | Trinh et al. |
| 5,670,475 A | 9/1997 | Trinh et al. |
| 5,698,166 A | 12/1997 | Vick et al. |
| 5,783,544 A | 7/1998 | Trinh et al. |
| 5,798,095 A * | 8/1998 | Racky .................... A61K 8/368 424/70.19 |
| 5,833,968 A * | 11/1998 | Keil ....................... A61K 8/60 424/70.17 |
| 5,861,128 A | 1/1999 | Vick et al. |
| 5,939,060 A | 8/1999 | Trinh et al. |
| 5,958,395 A * | 9/1999 | Kripp ..................... A61K 8/922 424/401 |
| 6,042,819 A * | 3/2000 | Karlen ................... A61K 8/895 424/70.1 |
| 6,077,318 A | 6/2000 | Trinh et al. |
| 6,146,621 A | 11/2000 | Trinh et al. |
| 6,213,358 B1 * | 4/2001 | Libit ................... B05B 11/0037 222/633 |
| 6,248,135 B1 | 6/2001 | Trinh et al. |
| 6,451,065 B2 | 9/2002 | Trinh et al. |
| 6,491,840 B1 * | 12/2002 | Frankenbach ........... C11D 1/62 252/8.61 |
| 6,938,805 B2 * | 9/2005 | Brincat .................... B65D 1/06 222/212 |
| 7,182,941 B2 | 2/2007 | Trinh et al. |
| 7,307,053 B2 | 12/2007 | Tasz et al. |
| 7,915,210 B2 | 3/2011 | Bennett et al. |
| 8,440,171 B2 | 5/2013 | Valpey, III et al. |
| 8,465,728 B2 | 6/2013 | Tasz et al. |

(Continued)

FOREIGN PATENT DOCUMENTS

| CN | 1611268 A | 5/2005 |
| CN | 103041426 A | 4/2013 |

(Continued)

OTHER PUBLICATIONS

English machine translation of JP05184650 (Year: 1993).*

*Primary Examiner* — Regina M Yoo
(74) *Attorney, Agent, or Firm* — S. C. Johnson & Son, Inc.

(57) ABSTRACT

Non-pressurized pump dispensable concentrated air freshener compositions, and a method of freshening air using a pump article containing a concentrated air freshener composition, are described. The air freshener compositions have a reduced VOC content and provide a fragrance intensity and longevity having at least parity with conventional pressurized air freshening aerosols.

19 Claims, 4 Drawing Sheets

(56) References Cited

U.S. PATENT DOCUMENTS

| | | | |
|---|---|---|---|
| 8,674,036 B2* | 3/2014 | Fukuhara | A61Q 5/06 525/474 |
| 8,691,301 B2 | 4/2014 | Seidling et al. | |
| 9,427,063 B2* | 8/2016 | Farrar | A45D 34/00 |
| 9,826,728 B2* | 11/2017 | Atarashi | A01N 29/02 |
| 2001/0054621 A1* | 12/2001 | Weber | B05B 11/3052 222/108 |
| 2004/0194800 A1 | 10/2004 | Chang et al. | |
| 2004/0223943 A1 | 11/2004 | Woo et al. | |
| 2005/0124512 A1 | 6/2005 | Woo et al. | |
| 2005/0229327 A1 | 10/2005 | Casella et al. | |
| 2006/0216214 A1 | 9/2006 | Brown et al. | |
| 2006/0228250 A1 | 10/2006 | Brown et al. | |
| 2007/0122373 A1 | 5/2007 | Woo et al. | |
| 2008/0003193 A1 | 1/2008 | Rebrovic | |
| 2008/0025942 A1 | 1/2008 | Weiss et al. | |
| 2008/0069780 A1 | 3/2008 | Weiss et al. | |
| 2008/0219934 A1* | 9/2008 | Kim | A61K 8/046 424/47 |
| 2009/0016966 A1 | 1/2009 | Anson et al. | |
| 2009/0130046 A1 | 5/2009 | Clark | |
| 2009/0257973 A1* | 10/2009 | Fraser | A61K 8/35 424/76.1 |
| 2010/0047353 A1* | 2/2010 | Batra | A61K 8/8147 424/489 |
| 2010/0135917 A1* | 6/2010 | Winter | A61K 8/8152 424/47 |
| 2010/0233098 A1 | 9/2010 | Bennett et al. | |
| 2011/0195037 A1 | 8/2011 | Berthier et al. | |
| 2011/0268667 A1 | 11/2011 | Woo et al. | |
| 2012/0097754 A1 | 4/2012 | Vlad et al. | |
| 2012/0134883 A1 | 5/2012 | Hecking | |
| 2012/0301421 A1 | 11/2012 | Hecking | |
| 2013/0011341 A1 | 1/2013 | Nguyen et al. | |
| 2013/0090283 A1 | 4/2013 | Guy | |
| 2013/0121930 A1 | 5/2013 | Boskamp | |
| 2013/0181013 A1 | 7/2013 | Tasz et al. | |
| 2013/0247931 A1* | 9/2013 | Fukuhara | A61Q 5/06 132/206 |
| 2013/0269830 A1* | 10/2013 | Farrar | A45D 34/00 141/27 |
| 2014/0024711 A1 | 1/2014 | Hedbom et al. | |
| 2015/0173342 A1* | 6/2015 | Atarashi | A01N 29/02 43/132.1 |
| 2015/0321828 A1* | 11/2015 | Neuhaus | B05B 11/3097 222/1 |

FOREIGN PATENT DOCUMENTS

| | | | | |
|---|---|---|---|---|
| JP | 05184650 | * | 7/1993 | A61L 9/01 |
| JP | 2004035461 A | | 2/2004 | |
| JP | 2006149892 A | | 6/2006 | |
| JP | 2010090317 A | | 4/2010 | |
| JP | 2012097367 A | | 5/2012 | |
| SU | 342627 A | | 4/1970 | |
| SU | 1437026 A1 | | 11/1988 | |

* cited by examiner

PUMP CONCENTRATED AIR FRESHENER

RELATED APPLICATION

This application claims benefit of U.S. Provisional Patent Application Nos. 61/972,115 filed Mar. 28, 2014 and 61/977,907 filed Apr. 10, 2014.

FIELD OF INVENTION

The invention is directed to non-pressurized pump dispensable concentrated air freshener compositions, and a method of freshening air using a pump article containing a concentrated air freshener composition. Pumps of particular interest are mini-pumps based on specific additional advantages obtained therewith.

BACKGROUND OF THE INVENTION

Air fresheners in the form of standard size aerosols (approximately 8 fluid ounces (236.5 ml) or greater) or small aerosols (up to about 6 fluid ounces (177.4 ml)) or mini-aerosols (generally 100 ml (3.38 fl. ozs.) or less) on the market currently are generally aerosols containing a liquefied petroleum gas (LPG), such as propane, butane or a mixture thereof. Mini-aerosols are generally used in metered dose automatic air freshener dispensers or as personal portable sprays. It is desirable to reduce the volatile organic compound (VOC) content of these air fresheners. Volatile organic compounds (VOCs) are organic chemicals that have a high vapor pressure at ordinary, room-temperature conditions. Their high vapor pressure results from a low boiling point, which causes large numbers of molecules to evaporate or sublimate from the liquid or solid form of the compound and enter the surrounding air. In the United States, different regulation exists per state. Considered probably the most restrictive is that of the California Air Resources Board (CARB). For consumer products, CARB regulations are set forth in the CARB publication entitled "Regulation For Reducing Volatile Organic Compound Emissions From Consumer Products", Subchapter 8.5, Consumer's Products, Article 2. One definition of a VOC is any organic compound (i.e., a compound containing at least one carbon atom in the molecule) that has a vapor pressure higher than 0.1 mmHg at 20° C. It is noted that the CARB regulations includes a listing of exceptions as to what qualifies as a VOC (see Article 2, § 94508(a)(144) of the "Regulation" publication noted above).

One alternative to the LPG-containing aerosols is the inclusion of compressed gas as the propellant rather than a LPG. While compressed gas is an alternative for standard size aerosol products for reducing VOC content, such is not suitable for use in mini-aerosol products since compressed gas formulations require too much head space volume, e.g., approximately 30 to 50%, which is not feasible in mini-aerosols. Further a suitable metered valve for a mini-aerosol which would work for dispensing a compressed gas aerosol product is not available.

Accordingly, a need exists to provide an alternative air freshener dispenser, especially a mini-air freshener dispenser, and composition having a reduced VOC content and yet still provide a fragrance intensity and longevity which is at least on par with, if not better than, conventional standard air freshening aerosols and mini aerosols.

SUMMARY OF THE INVENTION

The invention is directed to a dispenser in the form of a non-pressurized pump, a preferred embodiment being a mini-pump, and a concentrated air freshener composition providing for a longevity and intensity of fragrance on parity with or improved over conventional aerosol air fresheners. Non-pressurized pump dispenser or packaging as understood herein includes packaging that includes a pump and in which the pressure difference between the inside of the packaging and the outside of the packaging, if any, is small and is not introduced by the manufacturer. Liquid is dispensed through the action of the pump, which temporarily may compress a portion of the liquid. The terms "air freshener", "air freshener composition", "air freshener formulation", "air freshening composition" or variations thereof are considered equivalent herein and are understood to include air treating compositions which contain a fragrance and/or an odor elimination and/or sanitization active (such as, for example triethylene glycol (TEG) or propylene glycol) and/or a disinfectant (such as, for example, a quaternary ammonium compound). The air freshener composition of the invention is useful in treating both fabric (for example, upholstery, linens, etc.) and the air.

The pump concentrated air freshener of the invention does not require any head space volume for a propellant since no propellant is required in the air freshening formulation or pump dispenser. LPGs and compressed gas propellants are preferably excluded (in order to obtain most advantageous results) from formulations as described herein. These embodiments of the formulations have a significant reduced VOC content as compared to conventional aerosol air fresheners, whether present in a standard size aerosol container or a mini-aerosol container. It is noted, however, that the inclusion of a conventional LPG propellant in a pump formulation is not straightforward and can be problematic. It generally is not a consideration since reduced VOC content is a sought after goal. A LPG propellant can be filled into a pump container under the cup, but cannot be done through the valve. Pressurizing a plastic container requires a plastic that can withstand the pressure without collapsing. Further, pumps generally include a vent to equilibrate the pressure inside the container with external pressure to prevent collapse of the container. Thus, the vent may cause loss of propellant. However, a low boiling liquid, such as isopentane or neopentane is possible for inclusion in order to reduce particle sizes and increase the "burst" of plume.

It has been found that a pump container for dispensing an air freshener can have a reduced VOC content and a larger particle size as to the dispensed air freshener and still provide a sensory experience having an intensity and longevity on par with that provided in conventional standard sized aerosols and mini-aerosols for dispensing an air freshener. It has been further found that a mini-pump has significant advantages over conventional standard sized aerosols and mini-aerosols, in particular as to the degree of reduced VOC content and the ability to use a plastic container as a dispensing container as further described below.

In the invention, a preferred embodiment includes a small or mini-container, i.e., a small dispensing container having a content volume of greater than zero to about 6 fluid ounces (fl. ozs.)(177.4 ml) and a mini-dispensing container having a content volume of about 100 ml (3.38 fl. ozs.) or less. A correspondingly sized mini- or small pump head will be provided with the container for dispensing. The pump head can provide a spray at any desired angle depending on the use to which the mini-air freshener is to be put and may be a hand operated spray dispenser or an automatic or mechanical spray dispenser. Based on the air freshener formulation, the container can be and is preferably made of plastic, more preferably of clear plastic. The air freshener formulation can also be clear. Thus, when a clear air freshener formulation is contained in a clear plastic container, it can provide an appearance of purity to a consumer. Further, since a non-pressurized air freshener formulation does not require any head space for a propellant, the non-pressurized pump container can hold more product than an aerosol using the same size container, and a consumer can see the fill level of the container, i.e., that it is full and does not have an open head space.

The air freshening composition has a high level of fragrance therein and is considered a concentrated composition. Due to the absence of a propellant the composition has a reduced VOC content as compared to conventional air freshening aerosols. The composition further includes a high water content. The compositions are single phase.

A formulation of an air freshening composition of the invention for use in a pump dispenser, especially a mini-pump dispenser, includes about 30 to about 88 wt. % of water, about 10 to about 55 wt. % of an alcoholic solubilizing component, and about 2 to about 16 wt. % of a fragrance. Optional components includable in the concentrated air freshener are one or more actives, such as to provide for odor elimination and/or sanitization, present in an amount up to about 5 wt. %, one or more secondary solubilizers present in an amount up to about 1 wt. %, and one or more adjuvants, (such as a preservative) present in an amount up to about 0.5 wt. %.

The particle size of the dispensed composition may be generally within a range of about 25 to about 125 microns (this size being based on the particle distribution between the 10th and 90th percentiles of cumulative particle distribution).

It is surprising that a composition having a larger particle size is comparable to a LPG or compressed gas aerosol in terms of fragrance intensity and longevity since previously a pump spray air freshener of larger particle size was considered inferior in this regard and was not considered an option for use in dispensing an air freshener composition. This feature is further described below.

DETAILED DESCRIPTION OF THE INVENTION

The non-pressurized pump concentrated air freshener has a reduced VOC content and provides for a longevity and intensity of fragrance at least in parity with standard-sized aerosols and mini-aerosols containing LPG or compressed gas as the propellant component. This was previously considered not possible because of the particle size differential between aerosol and pump compositions. Now, however, the invention shows that parity as to fragrance intensity and longevity between aerosol and pump compositions is achievable. It is in particularly advantageous due to the pump dispensed composition having a reduced VOC content and as requiring no head space so allowing the provision of a full dispensing container at point of sale. It is in particularly advantageous as to mini-pump dispensers for air freshener compositions since previously no alternative to LPG mini-aerosols was available for air fresheners, especially for high fragrance content compositions.

Large pump dispensers are generally considered as being more than 6 fluid ounces, whereas small pump dispensing containers contain up to about 6 fluid ounces of content and include the subset of mini-pump dispensers which are considered as containing up to about 100 ml in content volume. Mini-pump dispensers due to their size have unique considerations over large and small dispensers. The containers preferably are made of plastic, preferably a thermoplastic material. Examples of thermoplastic materials suitable for use include ethylene based polymers, such as ethylene/vinyl acetate, ethylene acrylate, ethylene methacrylate, ethylene methyl acrylate, ethylene methyl methacrylate, ethylene vinyl acetate carbon monoxide, and ethylene N-butyl acrylate carbon monoxide, polybutene-1, high and low density polyethylene, polyethylene blends and chemically modified polyethylene, copolymers of ethylene and C1-C6 mono or di-unsaturated monomers, polyamides, polybutadiene rubber, polyesters such as polyethylene terephthalate, polyethylene naphthalate, polybutylene terephthalate; thermoplastic polycarbonates, atactic polyalphaolefms, including atactic polypropylene, polyvinylmethylether and others; thermoplastic polyacrylamides, polyacrylonitrile, copolymers of acrylonitrile and other monomers such as butadiene styrene; polymethyl pentene, polyphenylene sulfide, aromatic polyurethanes; styrene-acrylonitrile, acrylonitrile-butadiene-styrene, styrene-butadiene rubbers, acrylontrile-butadiene-styrene elastomers, polyphenylene sulfide, A-B, A-B-A, A-(B-A)$_n$-B, (A-B)$_n$-Y block polymers, wherein the A block comprises a polyvinyl aromatic block such as polystyrene, the B block comprises a rubbery midblock which can be polyisoprene, and optionally hydrogenated, such as polybutadiene, Y comprises a multivalent compound, and n is an integer of at least three, and mixtures of these substances. In particular embodiments, the thermoplastic material is polyethylene terephthalate (PET). PET is a readily available thermoplastic that is sold by many different manufactures. The thermoplastic polymer used to make the plastic container may be transparent, opaque, or partially opaque, with transparent being preferred. When the plastic is the preferred clear or transparent, the air freshener formulation also is preferably clear or transparent so as to provide an appearance of purity and visibility of fullness of the fill capacity of the container (due to no head space being present) when purchased. While plastic is preferred, it is possible to provide the container in conventional materials, e.g., metal, such as steel, aluminum, etc. With pressurized containers, plastic was not a viable option and the advantages of plastic are now available with the present invention and so it is much preferred. In using a plastic container, there is no concern as to corrosion of the container, and thus the need for including a corrosion inhibitor in the formula is eliminated.

Pump spray heads suitable for use will have a corresponding size to the pump container. So in the case of a mini-pump, the spray head will be a small size so as to be useful with and fit to the mini-pump dispensing container. Particle size will preferably be in a general range of about 25 to about 125 microns when measured between the 10th and 90th percentiles of cumulative particle distribution. Performance parameters for a pump dispensed concentrated air freshener composition have been found which provide for fragrance intensity and longevity on par with that of conventional aerosol air freshener compositions. The pump dispensed air freshener, however, has the additional advantages of reduced VOC content and greater fill capacity for the same size container when compared to an aerosol dispensed air freshener. The sensory advantages in relation to particle size is further set forth below as to inventive and comparative examples. The spray heads can be selected for dispensing at any angle, e.g., vertical or horizontal spray dispensing as well as angles therebetween. Further, the spray dispenser can operate either manually or automatically.

The air freshener formulations are concentrated in the sense of containing a high level or amount of fragrance. Due to the reduced VOC content of the formulations of the invention (based on not containing a propellant and having a reduced amount of solubilizer) a higher level of fragrance can be present in the formulations. This allows for parity or improvement in terms of longevity and intensity of the fragrance as compared to standard sized- or mini-aerosols which contain propellants.

The concentrated air freshener compositions of the invention are single phase. A formulation of a concentrated air freshener composition of the invention for dispensing from a non-pressurized pump dispensing container, especially for a mini-pump dispensing container, is generally as follows:

| Ingredient | Wt. % |
|---|---|
| Water | about 30 to about 88 |
| Alcoholic Solubilizing Component | about 10 to about 55 |
| Fragrance Component | about 2 to about 16 |

It is noted that as used herein "wt. %" is based on the total composition being based on 100 wt. %. Accordingly, the amount of the components of the formulation are selected so that total component amounts equal 100 wt. %.

The water serves as a carrier/solvent and can be deionized water, tap water, reverse osmosis water, and the like. Water is preferably present in an amount of about 30 to about 50 wt. %, more preferably about 30 to about 80 wt. %. Contrary to conventional practice, the more water that can be included in the formulation is the more preferred. Accordingly, the range provided above of about 30 to about 88 wt. % is the further more preferred.

The fragrance component can be a natural or synthetic fragrance which can be one or a mixture of fragrances. The fragrance component is preferably present in an amount of about 2 to about 12 wt. %, more preferably about 8 to about 12 wt. %.

The alcoholic solubilizing component can be one or more solubilizing components which will contain at least one alcohol group. The alcoholic solubilizing component preferably is a primary short chain ($C_1$-$C_4$) alcohol, but may also be a secondary short chain ($C_1$-$C_4$) alcohol, a ($C_1$-$C_4$) alkylene glycol, and the like. The alcoholic solubilizing component is preferably present in an amount of about 10 to about 55 wt. %, more preferably about 40 to about 50 wt. %. The alcoholic solubilizing component is preferably anhydrous, such as ethyl alcohol (anhydrous). However, the alcohol may also be a denatured alcohol, such as ethyl alcohol SDA40-B.

Other components which optionally can be present in the concentrated air freshener composition include the following:

| Ingredient | Wt. % |
|---|---|
| Odor Eliminator(s)/Sanitizers | up to about 5 |
| Secondary Solubilizing Component(s) | up to about 1 |
| Adjuvant(s) | up to about 0.5 |

Odor eliminators/sanitizers suitable for use include mono-, di- and tri-alkylene glycols, preferably triethylene glycol (TEG), propylene glycol and dipropylene glycol. The odor eliminator(s)/sanitizers are preferably present in an amount of about 0.5 to about 5 wt. %, more preferably about 1 to about 5 wt. %.

Secondary solubilizers include alcohol-containing compounds such as glycols, glycol monoethers, ketones and the like. Preferred secondary solubilizers suitable for use are propylene glycol, acetone, diethylene glycol monoethyl ether, and the like. Secondary solubilizers are preferably present in an amount of about 1 to about 15 wt. %, more preferably about 1 to about 5 wt. %.

Adjuvants suitable for use can include preservatives, and other adjuvants as conventionally usable in air fresheners. The adjuvant(s) are preferably present in an amount of about 0.05 to about 0.5 wt. % based on total adjuvant components present, more preferably about 0.05 to about 0.1 wt. %.

Surfactants are not a preferred included ingredient in the concentrated air freshener compositions of the invention. Surfactant(s) are only suitable for use when the fragrance is present in an amount up to about 4 wt. %. Surfactant(s) are generally necessary in compositions having low fragrance content levels (i.e., below 1 wt. %), such as in conventional aerosol air fresheners, in order to solubilize the fragrance. However, in compositions containing a higher level of fragrance of about 2 to about 16 wt. % such as in the present invention, in amounts greater than about 4 wt. %, the surfactant would be needed in an amount of at least as much percentage as the percentage of the fragrance present in order to solubilize the fragrance. This would result in a thickening of the composition to a degree that would not be beneficial for dispensing the air freshener from a pump container.

Examples of particular concentrated air freshener formulations of the invention are set forth below:

Examples 1(a)-(d)

| | Wt. % | | | |
|---|---|---|---|---|
| Ingredient | (a) | (b) | (c) | (d) |
| Deionized Water | 44.1 | 43.2 | 41.4 | 39.6 |
| Ethyl Alcohol Absolute (Anhydrous) | 53.9 | 52.8 | 50.6 | 48.4 |
| Fragrance | 2.0 | 4.0 | 8.0 | 12.00 |
| | 100 | 100 | 100 | 100 |

Example 2(a) to (d)

| Ingredient | Wt. % | | | |
|---|---|---|---|---|
| | (a) | (b) | (c) | (d) |
| Deionized Water | 44.055 | 43.155 | 41.355 | 39.555 |
| Ethyl Alcohol Absolute (Anhydrous) | 53.845 | 52.745 | 50.545 | 48.345 |
| Fragrance | 2.0 | 4.0 | 8.0 | 12.00 |
| Preservative (2-Methyl-4-isothiazolin-3-one (9.9%)) | 0.1 | 0.1 | 0.1 | 0.1 |
| | 100 | 100 | 100 | 100 |

Example 3(a) to (d)

| Ingredient | Wt. % | | | |
|---|---|---|---|---|
| | (a) | (b) | (c) | (d) |
| Deionized Water | 43.38 | 42.48 | 40.68 | 38.00 |
| Triethylene Glycol (98% pure) | 1.0 | 1.0 | 1.0 | 1.0 |
| Ethyl Alcohol Absolute (Anhydrous) | 53.02 | 51.92 | 49.72 | 48.4 |
| Fragrance | 2.0 | 4.0 | 8.0 | 12.0 |
| Propylene Glycol | 0.5 | 0.5 | 0.5 | 0.5 |
| Preservative (2-Methyl-4-isothiazolin-3-one (9.9%)) | 0.1 | 0.1 | 0.1 | 0.1 |
| | 100 | 100 | 100 | 100 |

To show that at least parity is present between air freshening formulations of the invention and a propellant-containing aerosol as to longevity and intensity, testing was conducted and the results obtained are as described below.

Test

Aerosol Formulations Tested—Examples 4(a)-(d)

| Ingredients | Wt. % | | | |
|---|---|---|---|---|
| | (a) | (b) | (c) | (d) |
| Ethyl Alcohol Absolute (Anhydrous) | 45.79 | 43.79 | 39.79 | 31.79 |
| Fragrance | 2.0 | 4.0 | 8.0 | 16.00 |
| Isobutane/Propane (70/30 wt. %) | 52.21 | 52.21 | 52.21 | 52.21 |
| | 100 | 100 | 100 | 100 |

Examples 4(a) and 4(c) were compared against inventive Examples 1(a) and 1(c) as set forth above.

The pump system and the aerosol system were each tested against each other using five different fragrances denoted as A, B, C, D and E. The fragrances were provided in amounts of 2 wt. % and 8 wt. % for each fragrance. The compositions were each then tested based on a single spray and double sprays as to longevity and intensity. The composition was also tested as to cumulative particle size distribution, i.e., to show the size of particles delivered.

The aerosol container used in the testing was a 55 mm high aluminum aerosol can of 12 mL capacity. The pump container used in the testing was a similarly sized plastic bottle.

As to the intensity and longevity testing, the same protocol was used to test both the pump versions and the aerosol versions as described. In this testing, the intensity, i.e., strength, of the fragrance was measured at the 5 minutes and 15 minutes point following spraying is shown in the graphs of FIGS. 1(a)-(e).

In FIGS. 1(a)-(e) along the horizontal axis, 1=2% formula sprayed once, 2=2% formula sprayed twice, 4=8% formula sprayed once, and 8=8% formula sprayed twice. The symbol designations as used in the graphs are the same for each graph. The sensory intensity results for the different fragrances of the aerosol and pump formulations are similar and do not contain any large gaps, thus, indicating parity as to sensory intensity.

In FIGS. 2(a)-(e), the intensity results as measured over time intervals following spraying are set forth. The time intervals were 5, 15, 30, 45, 60, 75, 90, 105 and 120 minutes. Again, similarity in intensity over time (longevity) as between the aerosol and the pump formulations are essentially the same, thus, indicating parity as to longevity.

Particle size distribution testing was conducted using a Malvern Spraytec particle size analyzer. The particle size distribution data was measured by spraying the test unit into the Malvern SprayTec instrument. The distance between the exit orifice of the unit and the laser beam was maintained at 3 to 4 inches. Data from three sprays were averaged and used in the calculation. For aerosol, the straight-through 0.020" orifice nozzle was used, as in the commercial holder. For pumps, a sprayer nozzle was used with mechanical break-up and 0.008" exit orifice. The samples for the Malvern Testing using 2 wt. % fragrance are set forth in Table 1 below. The samples for the Malvern Testing using 8 wt. % fragrance are shown in Table 2 below.

TABLE 1

| Malvern Testing - 2 Wt. % Fragrance | | | | |
|---|---|---|---|---|
| | Sample/Fragrance | Dv(10) | Dv(50) | Dv(90) |
| (1) | Aerosol-E | 13.76 | 27.26 | 49.55 |
| (2) | Pump-E | 25.15 | 54.83 | 122.84 |
| (3) | Aerosol-C | 14.03 | 26.74 | 49.06 |
| (4) | Pump-C | 29.31 | 62.04 | 126.18 |
| (5) | Aerosol-D | 14.41 | 29.84 | 56.81 |
| (6) | Pump-D | 28.10 | 58.11 | 115.52 |
| (7) | Aerosol-B | 13.84 | 26.46 | 46.48 |
| (8) | Pump-B | 24.88 | 50.04 | 96.62 |

TABLE 2

| Malvern Testing - 8 Wt. % Fragrance | | | | |
|---|---|---|---|---|
| | Sample/Fragrance | Dv(10) | Dv(50) | Dv(90) |
| (1) | Aerosol-E | 11.11 | 24.24 | 45.38 |
| (2) | Pump-E | 26.84 | 57.08 | 117.41 |
| (3) | Aerosol-C | 11.95 | 24.16 | 43.98 |
| (4) | Pump-C | 27.34 | 55.74 | 110.27 |
| (5) | Aerosol-D | 11.89 | 25.16 | 46.30 |
| (6) | Pump-D | 25.36 | 52.27 | 106.72 |
| (7) | Aerosol-B | 12.03 | 24.44 | 44.86 |
| (8) | Pump-B | 31.52 | 64.89 | 125.57 |

Figure 1A:
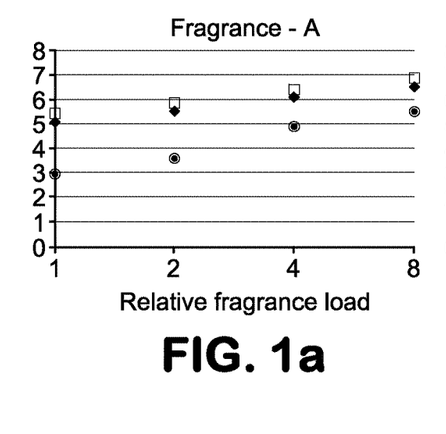
FIGS. 1(a)-(e) illustrate graphically sensory intensity testing results as to inventive air freshening compositions and comparative air freshening compositions.
Figure 1B:
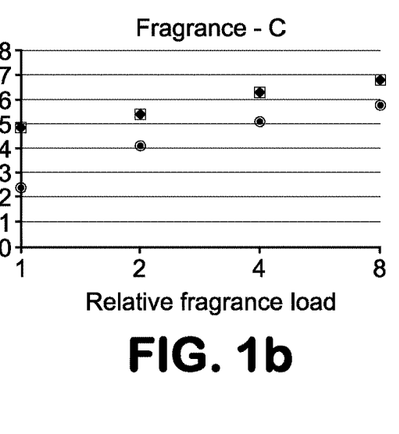
Figure 1C:
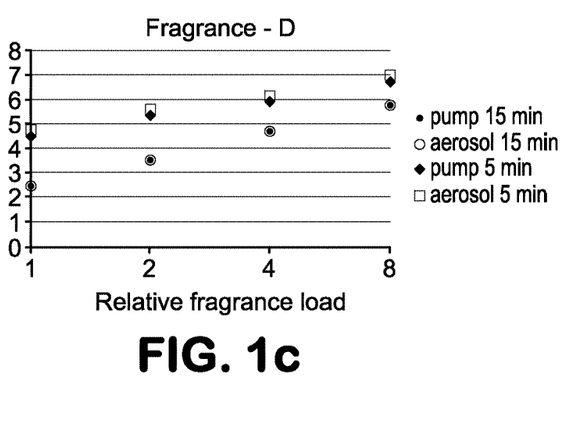
Figure 1D:
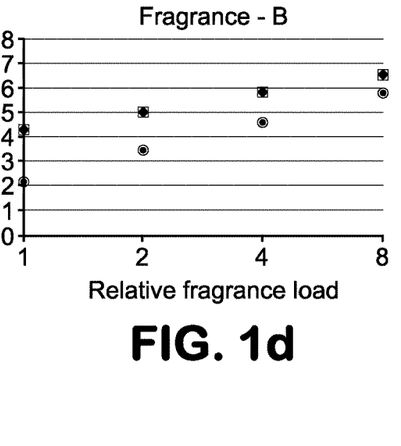
Figure 1E:
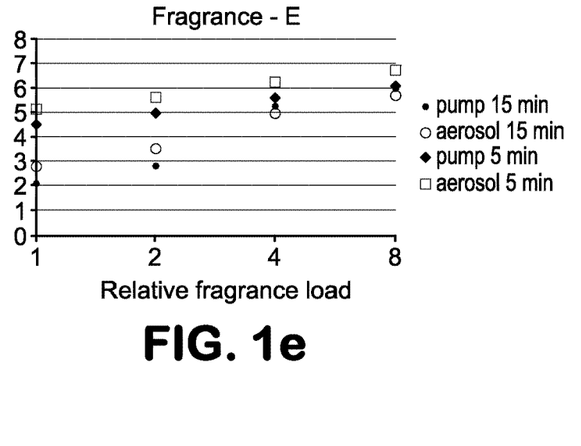
Figure 2A:
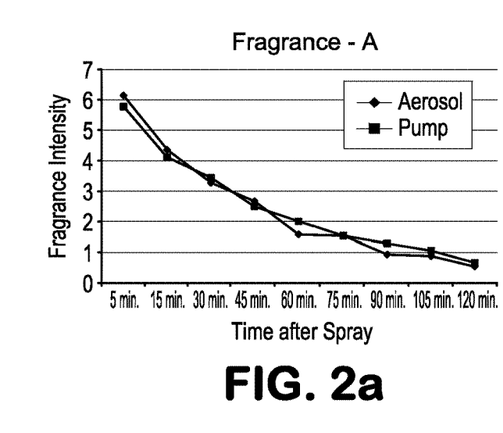
FIGS. 2(a)-(e) illustrate graphically sensory intensity results over time at different time intervals for inventive air freshening compositions and comparative air freshening compositions.
Figure 2B:
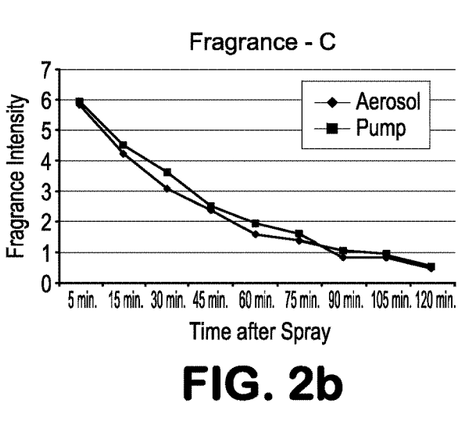
Figure 2C:
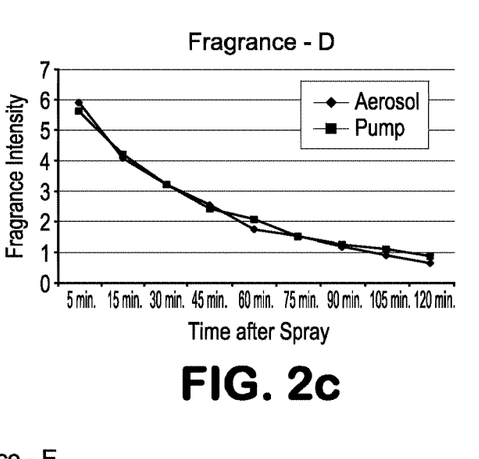
Figure 2D:
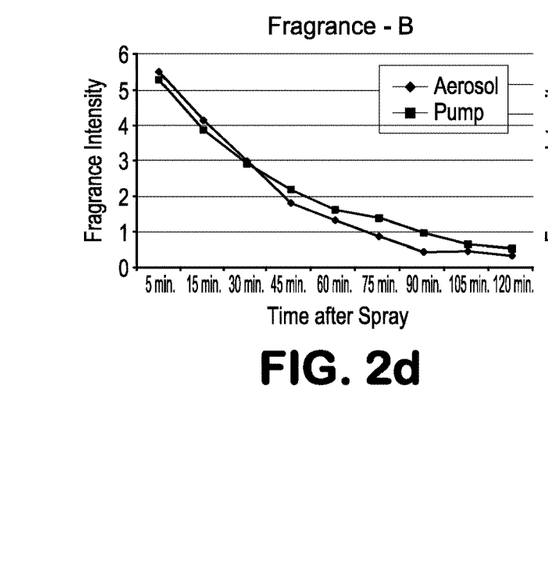
Figure 2E:
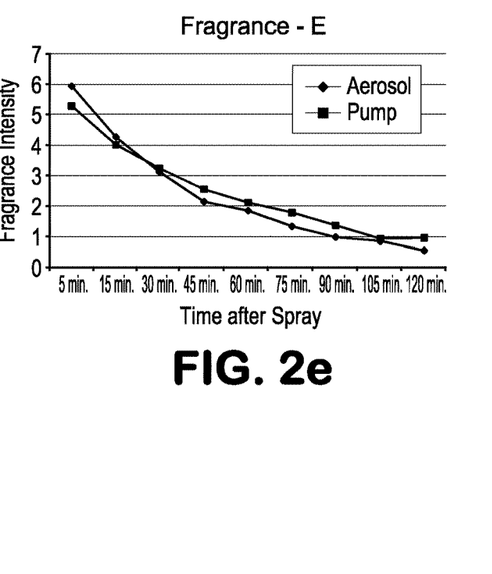
Figure 3:
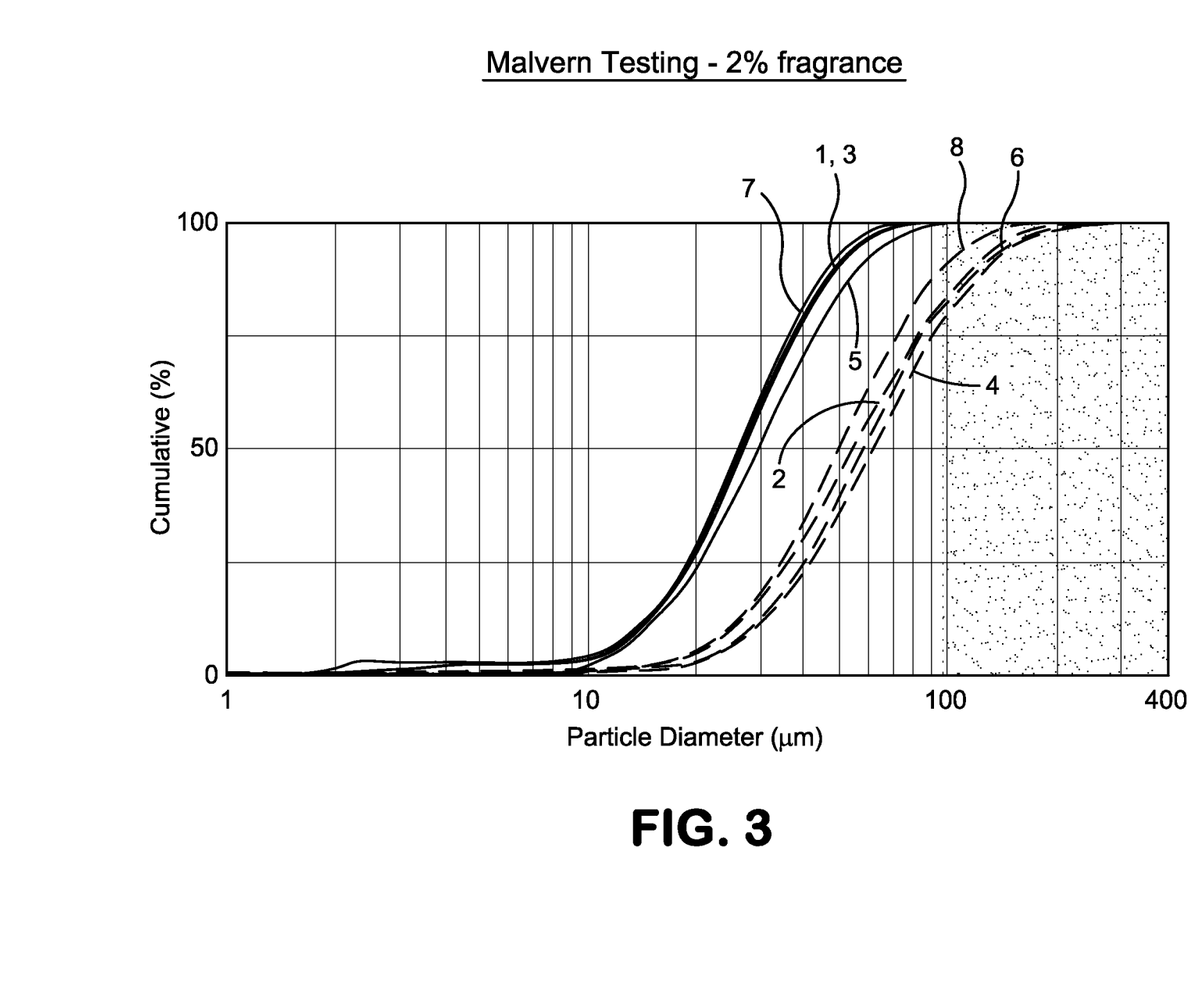
FIG. 3 is a graph illustrating the cumulative particle size distribution of Malvern Testing of four (4) fragrances at a 2 wt. % level for each of aerosol compositions and pump compositions.
Figure 4:
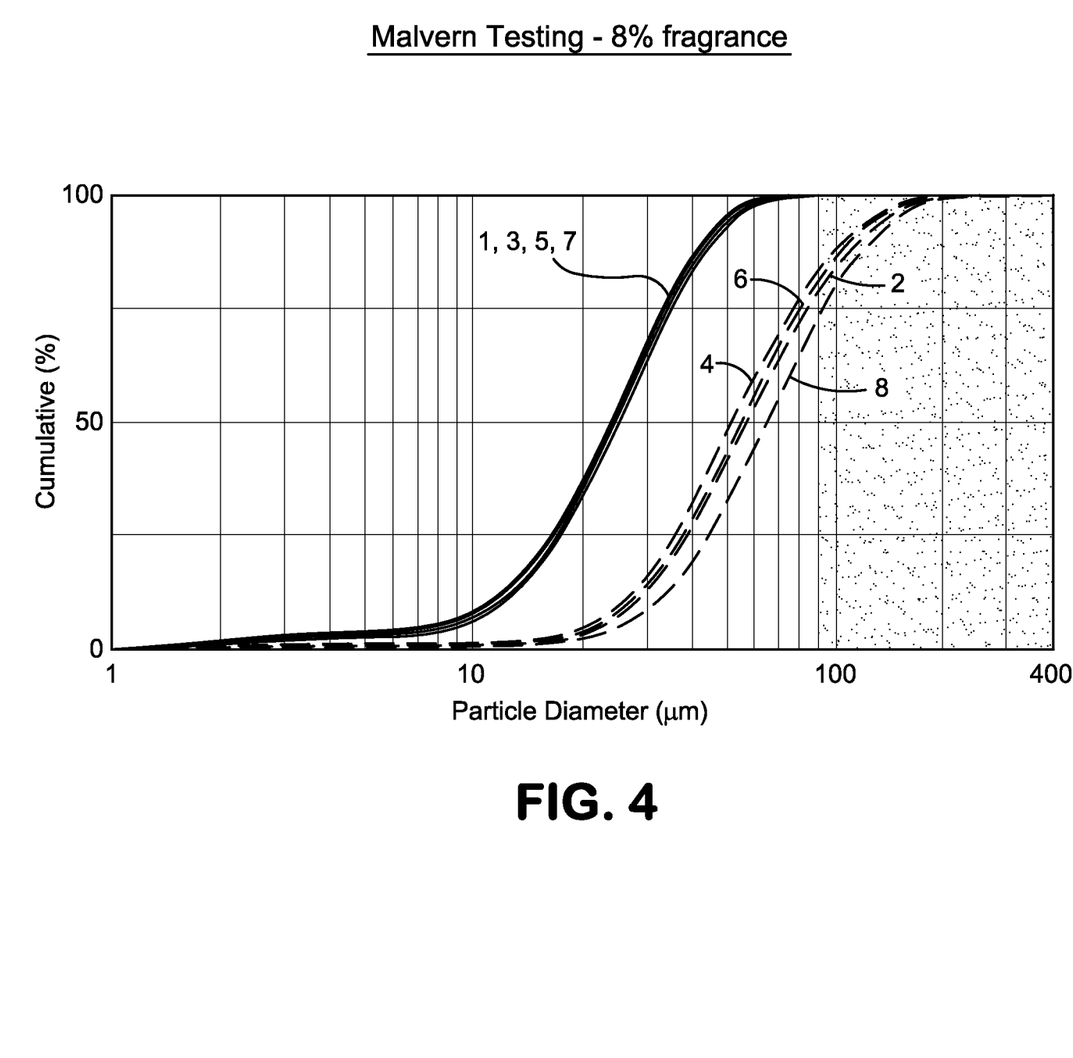
FIG. 4 is a graph illustrating the cumulative particle size distribution of Malvern Testing of four (4) fragrances at a level of 8 wt. % for each of aerosol compositions and pump compositions.

Dv(10), Dv(50) and Dv(90) indicate the particle diameter at 10% th, 50% th and 90% th percentile of spray volume distribution, respectively. The results are shown graphically in FIGS. 3 and 4. The solid lines in FIGS. 3 and 4 are the aerosol samples and the dotted lines indicate the pump samples. The numbers denoting the lines correspond to the sample numbers in Tables 1 and 2 above. The vertical lines between 10 and 100 on the horizontal (x)-axis increased by 10 (i.e., following 10 is 20, 30, 40, 50, 60, 70, 80, 90, 100). The vertical lines following 100 on the x-axis increase by 100. These results are further tabulated in Table 3 and 4 below.

TABLE 3

Aerosol Results

| Fragrance | Fragrance Conc. (Wt. %) | Delivery | Dv(50) (μm) |
|---|---|---|---|
| C | 2 | Aerosol | 26.7 |
| E | 2 | Aerosol | 27.4 |
| B | 2 | Aerosol | 26.6 |
| D | 2 | Aerosol | 29.8 |
| C | 8 | Aerosol | 24.0 |
| E | 8 | Aerosol | 24.2 |
| B | 8 | Aerosol | 24.5 |
| D | 8 | Aerosol | 25.2 |

Aerosol: Dv(50) = 26.1 ± 2.0 μm.

TABLE 4

Pump Results

| Fragrance | Fragrance Conc. (Wt. %) | Delivery | Dv(50) (μm) |
|---|---|---|---|
| C | 2 | Pump | 60.7 |
| E | 2 | Pump | 55.8 |
| B | 2 | Pump | 50.1 |
| D | 2 | Pump | 58.0 |
| D | 8 | Pump | 52.1 |
| C | 8 | Pump | 55.1 |
| E | 8 | Pump | 56.9 |
| B | 8 | Pump | 65.0 |

Pump: Dv(50) = 56.7 ± 4.7 μm.

Based on testing of two products, each tested with 4 fragrances, at 2 fragrance concentrations, it can be seen that no appreciable effect on spray diagnostics parameters is present as to fragrance formulation and concentration. When Dv(50) was larger in each case for the pump delivery compared to aerosol delivery, the pump still delivered a spray with fragrance intensity and longevity comparable to the aerosol sprays. Thus, the performance of the non-pressurized pump delivered concentrated air freshener and the propellant-containing aerosol air freshener are similar, and yet the non-pressurized pump delivered concentrated air freshener has the additional advantages of a reduced VOC content and ability to be dispensed from a plastic container (including its attendant advantages of transparency and greater fill capacity). Based on the results, the particle size of the pump dispensed composition can be approximately 1.5 to 3.0 times larger at Dv(50) as the aerosol spray particles and still have parity therewith.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. An air or fabric treatment system comprising, in combination, —
    (a) a composition for spraying air or fabric, for treatment thereof, consisting of, based on 100 wt. %, —
        (1) about 30 to about 88 wt. % water,
        (2) about 10 to about 55 wt. % of at least one alcoholic solubilizing agent,
        (3) about 2 to about 16 wt. % of a fragrance component,
        (4) optionally, up to about 5 wt. % of one or more of an odor eliminating component, a sanitizing component, or a mixture thereof,
        (5) optionally, up to about 1 wt. % of one or more secondary solubilizing agents, and
        (6) optionally up to about 0.5 wt. % of a preservative;
    (b) a non-pressurized spray pump container including a spray head and a body wherein said body holds said composition;
    wherein said composition when dispensed by said spray head has particle sizes in a range of about 25 to about 125 microns when measured between the 10th and 90th percentiles of cumulative particle distribution, and wherein a propellant is excluded from said composition.

2. The air or fabric treatment system of claim 1 wherein said composition is a single phase.

3. The air or fabric treatment system of claim 1 wherein said composition is clear.

4. The air or fabric treatment system of claim 1 wherein said body is about 6 fluid ounces or less in content volume.

5. The air or fabric treatment system of claim 4 wherein said body is about 100 milliliters (ml) or less in content volume.

6. The air or fabric treatment system of claim 5 wherein said body is made of plastic and is transparent, opaque or partially opaque.

7. The air or fabric treatment system of claim 1 wherein said body is made of plastic.

8. The air or fabric treatment system of claim 7 wherein said plastic is a thermoplastic material.

9. The air or fabric treatment system of claim 7 wherein said body is transparent or opaque or partially opaque.

10. The air or fabric treatment system of claim 9 wherein said body is transparent.

11. The air or fabric treatment system of claim 1 wherein particles provided by said spray head are about 1.5 to about 3 times in size larger at a particle diameter at the 50th percentile of spray volume distribution as compared to particles at Dv(50) of said composition when present as an aerosol spray.

12. The air or fabric treatment system of claim 1 wherein a surfactant is excluded from said composition when said fragrance component is present in an amount greater than 4 wt. %.

13. The air or fabric treatment system of claim 1 wherein said odor eliminating component and/or sanitizing component is present and is one or more of mono-, di- and tri-alkylene glycols, propylene glycol, dipropylene glycol, and a quaternary ammonium compound.

14. The air or fabric treatment system of claim 1 wherein said at least one alcoholic solubilizing agent is one or more of a primary C1-C4 alcohol, a secondary C1-C4 alcohol, and a C1-C4 alkylene glycol.

15. The air or fabric treatment system of claim 1 wherein said water is present in a range of about 30 to about 80 wt. %.

16. The air or fabric treatment system of claim 1 wherein said at least one alcoholic solubilizing agent is present in a range of about 40 to about 50 wt. %.

17. The air or fabric treatment system of claim 1 wherein said fragrance component is present in a range of about 8 to about 12 wt. %.

18. The air or fabric treatment system of claim 1 wherein at least one of said secondary solubilizing agents is present and selected from alcohol-containing compounds.

19. The air or fabric treatment system of claim 1 wherein said one or more of said odor eliminating component and said sanitizing component are present in a range of about 0.5 to about 5 wt. %.

* * * * *